United States Patent
Duan et al.

(10) Patent No.: US 10,219,750 B2
(45) Date of Patent: Mar. 5, 2019

(54) SYSTEM, METHOD AND RECORDING MEDIUM FOR DETERMINING A REMEDIATION ACTION

(71) Applicant: International Business Machines Corporation, Armonk, NY (US)

(72) Inventors: Ning Duan, Beijing (CN); Peng Gao, Beijing (CN); He Yuan Huang, Beijing (CN); Jingchang Huang, Shanghai (CN)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 115 days.

(21) Appl. No.: 15/282,456

(22) Filed: Sep. 30, 2016

(65) Prior Publication Data

US 2018/0092603 A1    Apr. 5, 2018

(51) Int. Cl.
| | |
|---|---|
| A61B 5/00 | (2006.01) |
| A61B 5/08 | (2006.01) |
| A61B 7/00 | (2006.01) |
| B60H 3/06 | (2006.01) |
| B60H 1/00 | (2006.01) |
| B60H 3/02 | (2006.01) |

(52) U.S. Cl.
CPC .......... *A61B 5/6893* (2013.01); *A61B 5/0022* (2013.01); *A61B 5/0823* (2013.01); *A61B 5/4803* (2013.01); *A61B 5/7246* (2013.01); *A61B 5/7282* (2013.01); *A61B 7/003* (2013.01); *B60H 1/008* (2013.01); *B60H 1/00742* (2013.01); *B60H 3/02* (2013.01); *B60H 3/06* (2013.01); *A61B 5/7264* (2013.01); *A61B 2503/22* (2013.01); *A61B 2560/0252* (2013.01); *A61B 2562/0204* (2013.01); *A61B 2562/029* (2013.01); *A61B 2562/0271* (2013.01); *G05B 2219/2614* (2013.01); *G05B 2219/2637* (2013.01)

(58) Field of Classification Search
CPC .. A61B 7/02; A61B 5/00; A61B 5/021; A61B 5/0476; A61B 5/0408; G10L 25/66; B60H 1/00; B60H 1/24; B60H 1/008; B60H 1/00764
USPC .......... 55/385.1, 472, 473, DIG. 34; 96/424, 96/397, 417, 422; 95/25, 26
See application file for complete search history.

(56) References Cited

U.S. PATENT DOCUMENTS

| | | | |
|---|---|---|---|
| 6,660,070 B2* | 12/2003 | Chung | B01D 46/008 96/424 |
| 2011/0184250 A1 | 7/2011 | Schmidt et al. | |

(Continued)

OTHER PUBLICATIONS

Peter Mel, et al., "The NIST Definition of Cloud Computing", IBM Confidential: Attorney Work Product; Nov. 2015, pp. 7-13.

*Primary Examiner* — Duane Smith
*Assistant Examiner* — Minh Chau T Pham
(74) *Attorney, Agent, or Firm* — Kevin M. Jordan, Esq.; McGinn IP Law Group, PLLC

(57) ABSTRACT

A method of determining a remediation action includes detecting an acoustic event in a vehicle, detecting an environmental condition in the vehicle, detecting a respiratory disease symptom of a passenger in the vehicle based on the detected acoustic event, correlating the detected respiratory disease symptom with the environmental condition in the vehicle, and determining a remediation action for the detected respiratory disease symptom.

20 Claims, 11 Drawing Sheets

(56) References Cited

U.S. PATENT DOCUMENTS

| | | |
|---|---|---|
| 2014/0309790 A1 | 10/2014 | Ricci |
| 2015/0032266 A1 | 1/2015 | Weast et al. |
| 2015/0052975 A1 | 2/2015 | Martin |
| 2017/0086778 A1* | 3/2017 | Cahan ..................... A61B 7/02 |
| 2017/0106715 A1* | 4/2017 | Duan ................. B60H 1/00764 |
| 2017/0313274 A1* | 11/2017 | Jeon ................. B60R 21/01542 |
| 2018/0009497 A1* | 1/2018 | Erickson .................. B62J 27/00 |
| 2018/0081428 A1* | 3/2018 | Liu ......................... G06F 3/013 |
| 2018/0085046 A1* | 3/2018 | Ashoori ............... A61B 5/4082 |
| 2018/0085630 A1* | 3/2018 | Capell ............... A63B 24/0075 |

\* cited by examiner

SYSTEM, METHOD AND RECORDING MEDIUM FOR DETERMINING A REMEDIATION ACTION

BACKGROUND

The present invention relates generally to a system and method for determining a remediation action, and more generally, but not by way of limitation, to a method of determining a remediation action based on a detected acoustic event and a detected environmental condition.

Chronic respiratory disease (CRD) triggers vary greatly from person-to-person. In many cases, it is very hard for an affected person to clearly identify a factor that induces CRD. Further, detection of a CRD-related condition typically requires specific testing, which is time-consuming, difficult and can be very expensive.

SUMMARY

An exemplary aspect of the present invention is directed to a computer-implemented method of determining a remediation action. The method includes detecting an acoustic event in a vehicle, detecting an environmental condition in the vehicle, detecting a respiratory disease symptom of a passenger in the vehicle based on the detected acoustic event, correlating the detected respiratory disease symptom with the environmental condition in the vehicle, and determining a remediation action for the detected respiratory disease symptom.

Another exemplary aspect of the present invention is directed to a system for determining a remediation action. The system includes an acoustic event detector for detecting an acoustic event in vehicle, an environmental condition detector for detecting an environmental condition, and a remediation action determining device for detecting a respiratory disease symptom of a passenger in the vehicle based on the detected acoustic event, correlating the detected respiratory disease symptom with the environmental condition in the vehicle, and determining a remediation action for the detected respiratory disease symptom.

Another exemplary aspect of the present invention is directed to a computer readable storage medium storing a program of instructions executable by a machine to perform a method of determining a remediation action. The method includes detecting an acoustic event in a vehicle, detecting an environmental condition in the vehicle, detecting a respiratory disease symptom of a passenger in the vehicle based on the detected acoustic event, correlating the detected respiratory disease symptom with the environmental condition in the vehicle, and determining a remediation action for the detected respiratory disease symptom.

BRIEF DESCRIPTION OF THE DRAWINGS

The exemplary aspects of the present invention will be better understood from the following detailed description of the exemplary embodiments of the invention with reference to the drawings, in which.

DETAILED DESCRIPTION

Figure 1:
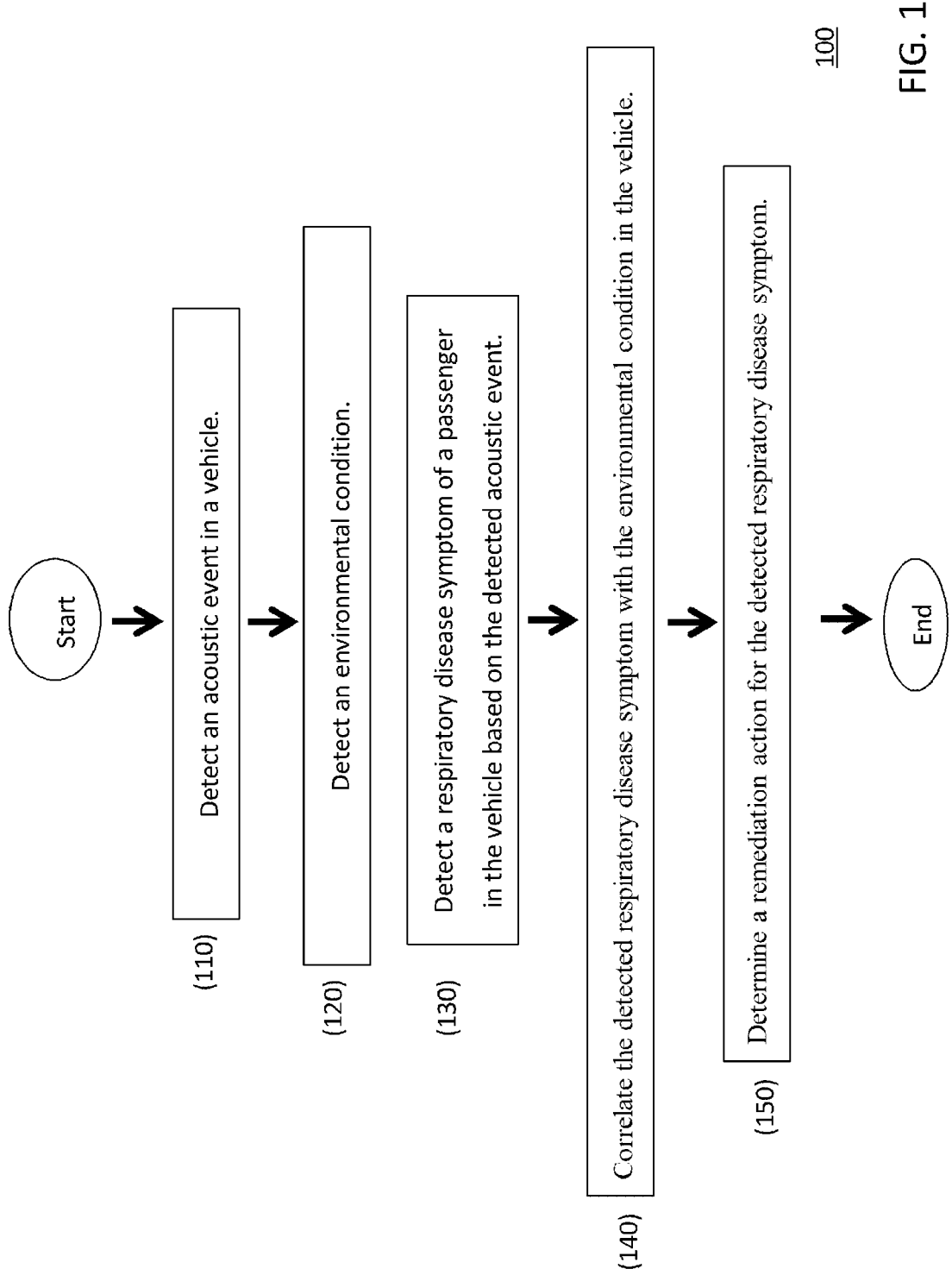
FIG. 1 illustrates a method 100 of determining a remediation action, according to an exemplary aspect of the present invention.

The invention will now be described with reference to FIGS. 1-11, in which like reference numerals refer to like parts throughout. It is emphasized that, according to common practice, the various features of the drawing are not necessarily to scale. On the contrary, the dimensions of the various features can be arbitrarily expanded or reduced for clarity. Exemplary embodiments are provided below for illustration purposes and do not limit the claims.

A problem with conventional systems and methods, is that they do not determine a remediation action based on a detected acoustic event in a vehicle, and a detected environmental condition. Therefore, conventional systems and methods are not helpful in alleviating or stopping a symptom (e.g., CRD) symptom) of a passenger in the vehicle.

In contrast, the exemplary aspects of the present invention determines a remediation action based on a detected acoustic event in the vehicle, and a detected environmental condition, and may, therefore, help to alleviate or stop a symptom (e.g., a CRD symptom) of a passenger in the vehicle.

In particular, an exemplary aspect of the present invention may utilize vehicular space which has advantages for recognizing sound context accurately and detecting environment air quality sensitively, and thus is more practical than conventional systems and methods. Further, an exemplary aspect of the present invention may show the passenger how their health/wellness condition is associated with air quality in the vehicle, and may provide advice to the passenger on managing their health/wellness condition.

Further, an exemplary aspect of the present invention may recognize a chronic symptom of a person (e.g., passenger) and determine (e.g., simultaneously determine) a corresponding environment trigger simultaneously. This may allow the system to make a personalized recommendation for optimizing environment air quality (e.g., air quality in the vehicle). Thus, in short, an exemplary aspect of the present invention may use acoustic analytics to detect respiratory disease symptoms and correlate the symptoms with air quality in-vehicle, to recommend some remediation actions for a passenger.

With reference now to FIG. 1, a method 100 (e.g., computer-implemented method) according to an exemplary aspect of the present invention includes various steps to determine a remediation action. One or more computers of a computer system according to an embodiment of the present invention can include a memory having instructions stored in a storage system to perform the steps of FIG. 1.

Thus, the method 100 of determining a remediation action according to an exemplary aspect of the present invention may act in a more sophisticated and useful fashion, and in a cognitive manner while giving the impression of cognitive mental abilities and processes related to knowledge, attention, memory, judgment and evaluation, reasoning, and advanced computation. That is, a system is said to be "cognitive" if it possesses macro-scale properties—perception, goal-oriented behavior, learning/memory and action—that characterize systems (i.e., humans) that are generally agreed as cognitive.

Figure 10:
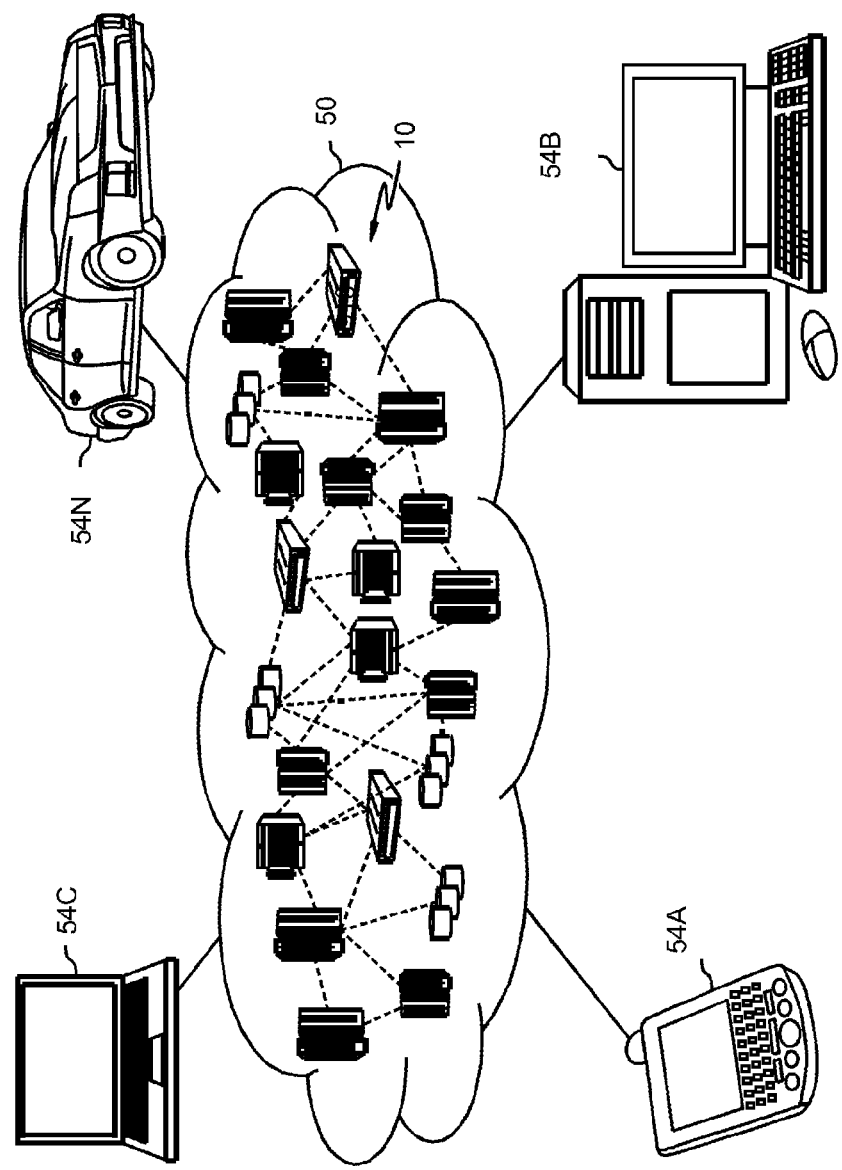
FIG. 10 depicts a cloud computing environment 50 according to an exemplary aspect of the present invention.

As will described/illustrated herein, one or more embodiments of the present invention (see e.g., FIGS. 1-8) may be implemented in a cloud environment 50 (see e.g., FIG. 10). It is nonetheless understood that the present invention can be implemented outside of the cloud environment.

Referring again to FIG. 1, the method of determining a remediation action 100 includes detecting (110) an acoustic event in a vehicle, detecting (120) an environmental condition in the vehicle, detecting (130) a respiratory disease symptom of a passenger in the vehicle based on the detected acoustic event, correlating (140) the detected respiratory disease symptom with the environmental condition in the vehicle, and determining (150) a remediation action for the detected respiratory disease symptom (e.g., an action for alleviating the symptom, such as stopping a cough, etc.).

The term "vehicle" as used herein is not necessarily limited to an automobile, but instead may be broadly considered to mean a device having a climate-controlled space (e.g., airplane, train, bus, boat cabin, etc.) which is smaller than 200 cubic feet.

The determining of the remediation action includes determining a remediation action for remedying the respiratory disease symptom. For example, if the symptom is a cough, then the remediation action is an action which alleviates (e.g., makes less severe or stops) the cough. If the symptom is a scratchy voice, then remediation action is an action which alleviates (e.g., makes less severe or stops) the scratchy voice. The method 100 may, therefore, determine the effectiveness of the remediation action by using an acoustic event detector (e.g., microphone) to determine whether the cough or scratchy voice has been alleviated (e.g., made less severe or stopped).

In an exemplary aspect of the present invention, the detecting (110) of the acoustic event may include detecting the acoustic event originating from a passenger of the vehicle, and the determining (130) of the remediation action may include determining a remediation action for the passenger of the vehicle. The detected acoustic event may include, for example, the passenger coughing, the passenger sneezing, the passenger wheezing, the passenger sniffing and the passenger clearing his throat, the passenger using a nasally voice, the passenger taking shallow breaths, and the passenger taking deep breaths.

The detecting (110) of the acoustic event may be performed, for example, by an acoustic event detector which includes an audio sensor, and the detecting 120 of the environmental condition may be performed in response to the acoustic event detector detecting the acoustic event.

Further, the detecting (120) of the environmental condition may include detecting an amount of particulate matter (PM) in air in the vehicle, an amount of volatile organic compounds (VOCs) in the air, a humidity in the air and a temperature of the air, and the detecting of the environmental condition may be performed by an environmental condition detector comprising one of a PM sensor, a VOC sensor, a humidity sensor and a temperature sensor.

The method 100 may also include, for example, recommending the determined remediation action to the passenger (e.g., based on a correlation between the detected respiratory disease symptom and the environmental condition in the vehicle), tracking an effect of the remediation action on acoustic events detected, and refining a remediation action determination based on the tracking of the effect of the remediation action.

The recommended remediation action may include, for example, increasing or decreasing the temperature in the vehicle, increasing or decreasing the humidity in the vehicle, decreasing the amount of PM in the vehicle, decreasing the amount of VOCs in the vehicle, and so on.

The method 100 may also include managing an air quality in the vehicle based on the recommended remediation action. The air quality may be managed, for example, by adjusting (e.g., decreasing) the amount of PM in the air in the vehicle, adjusting (e.g., decreasing) the amount of VOCs in the air, adjusting a humidity in the air, adjusting a temperature of the air, and so on.

In an exemplary aspect, the managing of the air quality may be performed by an air quality manager which is formed in a heating and cooling system of the vehicle.

The method 100 may also include storing (e.g., in a passenger profile database) a passenger profile which relates the determined remediation action with passenger information of the passenger (e.g., information indicating that passenger has CRD, passenger is sensitive to PM, passenger is sensitive to humidity, etc.). In this case, the air quality in the vehicle may be managed based on the passenger profile.

Figure 2:
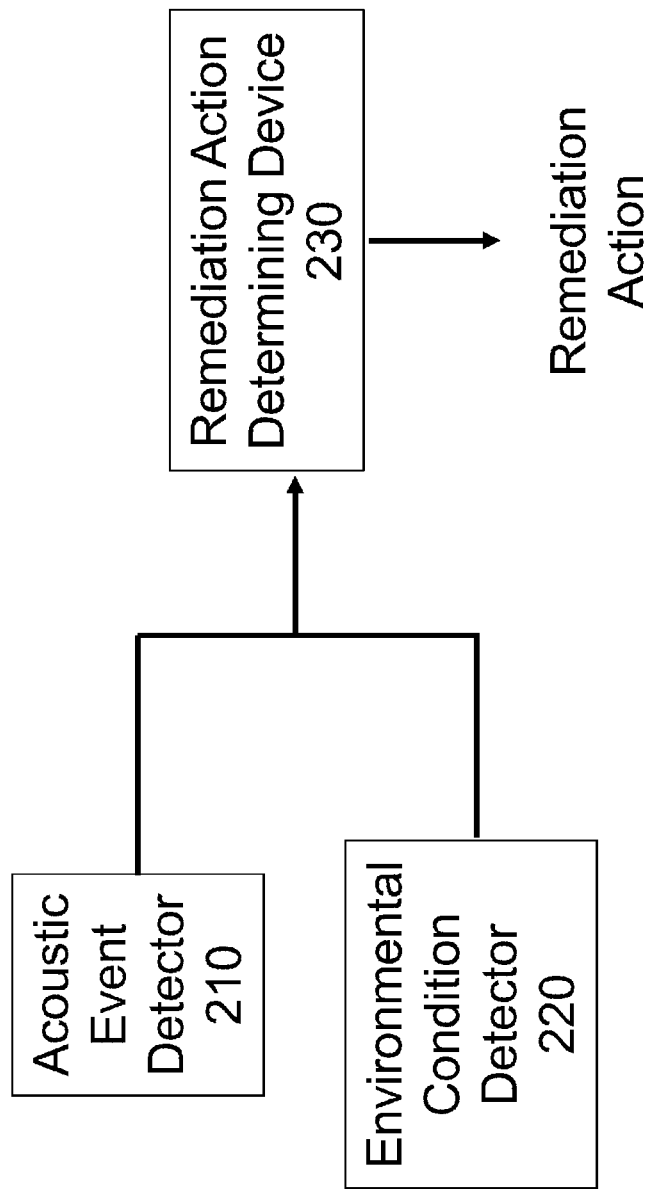
FIG. 2 illustrates a block diagram 200 for determining a remediation action according to an exemplary aspect of the present invention.

Referring again to the drawings, FIG. 2 illustrates a block diagram of a system 200 for determining a remediation action according to an exemplary aspect of the present invention. The system 200 may be used, for example, to implement the method 100.

As illustrated in FIG. 2, the system 200 includes an acoustic event detector 210 for detecting an acoustic event in a vehicle (e.g., a passenger coughing, the passenger sneezing, the passenger wheezing, the passenger sniffing and the passenger clearing his throat, the passenger using a nasally voice, the passenger taking shallow breaths, and the passenger taking deep breaths), an environmental condition detector 220 for detecting an environmental condition (e.g., an amount of PM in the air, an amount of VOCs in the air, a humidity in the air and a temperature of the air), and an remediation action determining device 230 for detecting a respiratory disease symptom of a passenger in the vehicle based on the detected acoustic event, correlating the detected respiratory disease symptom with the environmental condition in the vehicle, and determining a remediation action for the detected respiratory disease symptom (e.g., an action for alleviating the symptom, such as stopping a cough, etc.).

In an exemplary aspect, the acoustic event detector 210 includes a microphone—a sound sensor that converts a sound signal (e.g., sound wave) into a voltage or current proportional to the detected signal. The microphone may include a small diaphragm (e.g., magnets) surrounded by coiled metal wire. Sound waves cause the diaphragm to vibrate, vibrating the magnets and inducing a current in the coil. The audio sensor may also (or alternatively) include an electrostatic sensor or piezoelectric sensor (e.g., high-frequency ultrasonic sound sensor) which can detect sound pressure waves that are not within the audible range.

Risk factors of CRD include, for example, humidity, temperature, wind, PM2.5, VOC, etc., and risk factors of asthma include humidity, temperature, air pollutants, pollen, etc.

Table 1 below is a list of data obtained from a study of air pollution and COPD hospital admissions in Hong Kong.

TABLE 1

| Lag days | $NO_2$ | $PM_{10}$ | $O_3$ (8 h) | $SO_2$ | $PM_{2.5}$ |
|---|---|---|---|---|---|
| Lag 0   | 1.009 (1.005 to 1.013)** | 1.003 (1.000 to 1.005)*  | 1.002 (0.998 to 1.005)   | 1.007 (1.001 to 1.014)* | 1.002 (0.998 to 1.001) |
| Lag 1   | 1.001 (0.997 to 1.005)   | 1.005 (1.002 to 1.007)** | 1.011 (1.008 to 1.015)** | 0.991 (0.981 to 1.001)  | 1.003 (0.999 to 1.007)** |
| Lag 2   | 1.003 (0.999 to 1.007)   | 1.010 (1.007 to 1.012)** | 1.011 (1.008 to 1.020)** | 0.992 (0.935 to 1.000)  | 1.011 (1.007 to 1.014)** |
| Lag 3   | 1.010 (1.007 to 1.014)** | 1.051 (1.008 to 1.013)** | 1.011 (1.012 to 1.019)** | 1.006 (0.999 to 1.013)  | 1.013 (1.010 to 1.017)** |
| Lag 4   | 1.010 (1.007 to 1.014)** | 1.008 (1.006 to 1.011)** | 1.011 (1.008 to 1.015)** | 1.004 (0.998 to 1.011)  | 1.011 (1.008 to 1.015)** |
| Lag 5   | 1.008 (1.004 to 1.012)** | 1.007 (1.004 to 1.009)** | 1.006 (1.003 to 1.010)** | 1.004 (0.997 to 1.010)  | 1.009 (1.006 to 1.013)** |
| Lag 0-1 | 1.007 (1.003 to 1.011)** | 1.005 (1.002 to 1.008)** | 1.011 (1.006 to 1.014)** | 0.998 (0.991 to 1.006)  | 1.004 (0.999 to 1.008) |
| Lag 0-2 | 1.009 (1.004 to 1.013)** | 1.011 (1.008 to 1.014)** | 1.019 (1.015 to 1.023)** | 0.993 (0.985 to 1.001)  | 1.010 (1.006 to 1.015)** |
| Lag 0-3 | 1.026 (1.022 to 1.031)** | 1.016 (1.013 to 1.019)** | 1.027 (1.02 to 1.031)**  | 0.998 (0.989 to 1.007)  | 1.018 (1.013 to 1.022)** |
| Lag 0-4 | 1.021 (1.017 to 1.026)** | 1.020 (1.017 to 1.024)   | 1.031 (1.027 to 1.036)** | 1.001 (0.991 to 1.010)  | 1.024 (1.019 to 1.029)** |
| Lag 0-5 | 1.026 (1.022 to 1.031)** | 1.024 (1.021 to 1.028)** | 1.034 (1.030 to 1.040)** | 1.004 (0.994 to 1.014)  | 1.031 (1.026 to 1.036)** |

In an exemplary aspect, the environmental condition detector 220 includes a PM sensor, a VOC sensor, a humidity sensor, or a temperature sensor. The PM sensor may include, for example, an opacity monitor which measures the degree to which PM reduces the transmission of light, a light-scattering sensor which provides an indirect measurement of fine PM concentrations by utilizing the relationship between particle concentration and light scattering, a beta gauge which uses a radioactive source and measures the attenuation of radiation through an exposed filter, an acoustic energy monitor which measures particle loading by measuring shock waves caused by the impact of particles with a probe inserted into a flow (e.g., a flow of ambient air), a tapered-element oscillating microbalance (TEOM) which directly measures PM mass by measuring the changing frequency of oscillation of a filter as it accumulates particles, or triboelectric sensor which measures the electric current induced by particles as they flow past and hit a metal probe.

The VOC sensor may include, for example, a photoionization detector (PID), an infrared sensor, a flame ionization detector, or a gas sensitive semiconductor (GSS) sensor (e.g., a mixed metal oxide semiconductor sensor). The humidity sensor may include, for example, an electronic hygrometer which employs a capacitive sensing principle or a resistive sensing principle. The temperature sensor may include, for example, a digital thermometer (e.g., thermistor) including a sensor having a resistance which changes in response to a change in temperature.

It should be noted that in a case the acoustic event detector 210 or the environmental condition detector 220 may be a part of another device in a vehicle. For example, the environmental condition detector 220 may utilize a temperature sensor which is part of the vehicle's heating and cooling system. In this case, the environmental condition detector 220 may "detect" a temperature of the air in the vehicle by accessing temperature data which was previously obtained (e.g., and stored) by the vehicle's heating and cooling system.

The exemplary aspects of the present invention may help to alleviate the harmful effects of pollution (e.g., deterioration of the environment) which has become a leading threat and public concern to human health. Many diseases have been proven to be closely related or triggered by pollution. For example, chronic respiratory diseases (CRD) such as COPD have been shown to be exacerbated by air pollution.

The data is based on emergency hospital admissions for COPD in 15 major hospitals from January 2000 to December 2005. The data indicates the relative risk (with 95% confidence interval (CI)) for various pollutants per 10 μg/m³ increase in the concentration of air pollutants for hospitalizations due to an acute exacerbation of COPD (single pollutant model).

As illustrated in Table 1, an increase in pollutants was associated with an increase in hospital admissions for acute exacerbations of COPD. For example, the table indicates that a 10 μg/m³ increase in the concentration of $PM_{2.5}$ was associated with a 3.1% increase in hospital admissions for acute exacerbations of COPD at cumulative lag days of 0-5.

Figure 3:
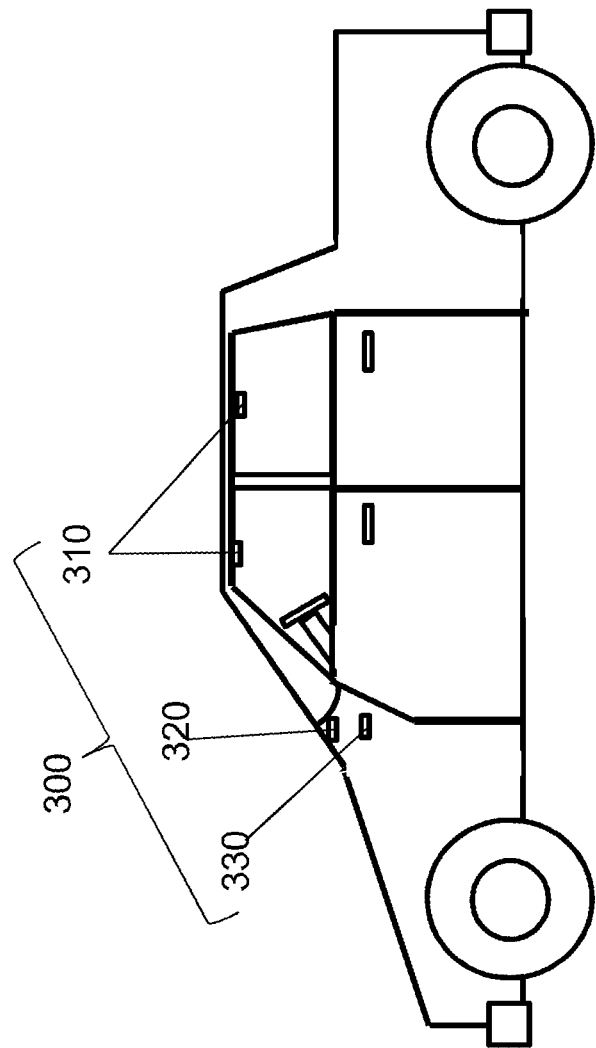
FIG. 3 illustrates an embodiment of a system 300 for determining a remediation action, according to another exemplary aspect of the present invention.

FIG. 3 illustrates another embodiment of a system 300 for determining a remediation action, according to another exemplary aspect of the present invention.

As illustrated in FIG. 3, the system 300 is similar to the system 200 (i.e., the acoustic event detector 310, environmental condition detector 320 and remediation action determining device 330 correspond to the acoustic event detector 210, environmental condition detector 220 and remediation action determining device 230 described above, respectively), and is implemented in the vehicle. Although, the vehicle illustrated in FIG. 3 is an automobile, the vehicle could be another type of vehicle such as, for example, an airplane, train, bus, etc.

The placement in FIG. 3 of the acoustic event detector 310, environmental condition detector 320 and remediation action determining device 330 is only illustrative and should not be considered as limiting in any manner. In particular, the acoustic event detector 310 (e.g., microphone) may include a plurality of acoustic event detectors 310 that are formed in a location proximate to a passenger's chest and/or head. For example, a passenger in the front passenger seat may be assigned a first acoustic event detector 310 in the ceiling about the front passenger seat, a second acoustic event detector 310 in the dashboard near the front passenger seat, and so on. The driver may be assigned a first acoustic event detector 310 in the ceiling about the driver seat, a second acoustic event detector 310 formed in the steering wheel, and so on. The acoustic event detector 310 may also be formed in the back portion of a passenger seat so that it is very close to the passenger's chest, and may be especially effective at detecting coughs, labored breathing, etc. when the passenger is seated in the seat with his back is pressed against the back of the passenger seat.

The environmental condition detector 320 and acoustic event detector 310 may be connected to the remediation action determining device 330 by wire or wireless (e.g., bluetooth signal). The remediation action determining device 330 may be formed, for example, as part of the vehicles electronic control unit (ECU). Alternatively, one or more features of the remediation action determining device 330 may be located remotely from the vehicle (e.g., on a remote server).

The system 300 may identify a correlation between CRD and the in-vehicle environment, and then provide personalized recommendation to protect a susceptible population. The vehicular environment includes a lot of advantages for experimentation. For example, the vehicle has a small space which aids with acoustic recognition and sensor performance.

The vehicle also provides a diverse seasonal and geographic environment, and affects near daily life with normal usage. Thus, the in-vehicle environment may serve as a "testbed" to study the correlation relationship between respiratory symptoms and sound. Technical speaking, the system 300 may use acoustic technologies to recognize a symptom (e.g., a CRD symptom) inside the vehicle, and then identify a correlation between CRD and the in-vehicle air environment. That is, the system 300 may profile in car CRD demographic information with acoustic analysis and Internet of Things (IoT) air sensor data analysis, and identify a correlation between CRD and the in-vehicle environment. The system 300 may then analyze the correlation, to provide a personalized recommendation which can be used to protect a susceptible population.

The invention may exploit the fact that CRD has strong a correlation with voice features, such as coughing, sneezing, etc. Further, CRD is impacted by many factors (e.g., humidity, temperature, etc.), and the effect of these factors on CRD may be unique to each individual. That is, there may be no common rule that can be used to describe how these factors affect people.

Patients with respiratory diseases are sensitive to environment triggers. For example, the possible environmental triggers for asthma include: indoor allergens (e.g., dust mites in bedding, carpets and stuffed furniture, pollution and pet dander), outdoor allergens (e.g., pollens and molds), tobacco smoke, chemical irritants in the workplace, air pollution, cold air, etc. Meanwhile, triggers/symptoms vary in severity and frequency from patient to patient. Even after a hospital visit, a patient with respiratory disease may not know the triggers to which he should pay attention. An exemplary aspect of the present invention may provide a dynamic and personalized recommendation to these patients with respiratory diseases.

Further, an in-vehicle environment can provide following benefit for creating a personalized remediation action for a passenger. The vehicle provides a small space which is beneficial for both acoustics and sensing. It also may provide a diverse environment, considering that the passenger is in the vehicle during different seasons and in different locations (e.g., in the country where there may be pollen in the air, in an industrial area where there may be pollutants such as $SO_2$, and so on). Further, the vehicle (especially where the vehicle is an automobile) may be used almost daily, and there may be no extra cost to the user to use the vehicle for determining the remediation action.

That is, the system 300 may utilize the vehicle as a cognitive environment. The vehicle cabin may be used as a test environment to determine the remediation action for a passenger in the vehicle, and support more cognitive solutions.

Figure 4:
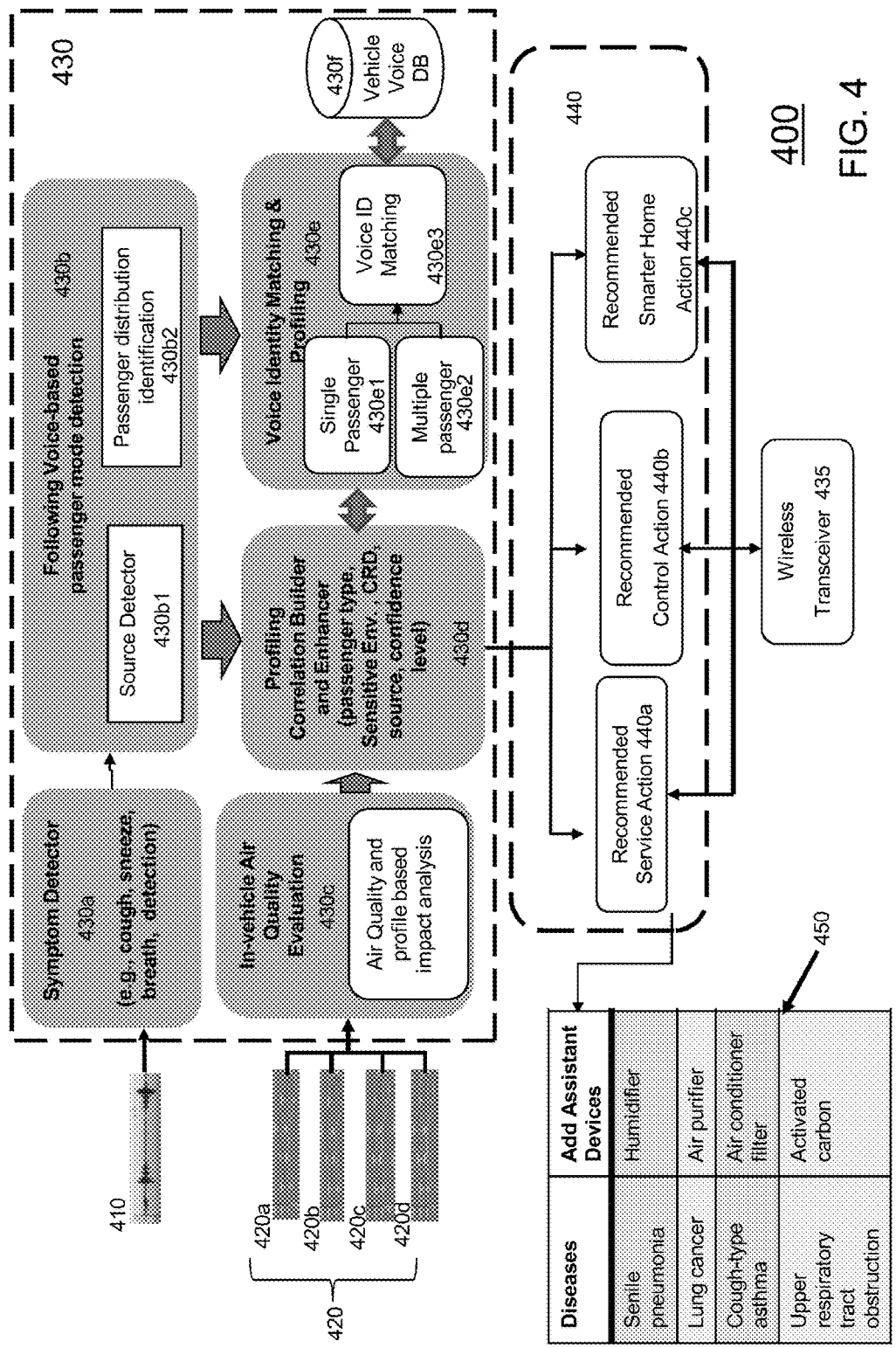
FIG. 4 illustrates a more detailed embodiment of the system depicted in FIG. 3, in accordance with the present invention.

Referring again to the drawings, FIG. 4 illustrates a system 400 for determining a remediation action, according to another exemplary aspect of the present invention.

The system 400 may provide an approach to monitoring a passenger's symptoms (e.g., coughing wheezing, etc.) that may be detected automatically by acoustic analysis. At the time that an acoustic event (e.g., a symptom) is detected, the system 400 may collect data on the corresponding environment (air quality, temperature, humidity, etc.) to identify the source (e.g., high amount of particulate matter in the air in the vehicle, low temperature of the air, etc.) of the passenger's symptoms. This approach may allow the system 400 to leverage the uniqueness of vehicle's cabin (e.g., a small space which is relatively climate-controlled and air tight) to provide an accurate result (e.g., recommended remediation action). Thus, the vehicle may serve as a test bed which is practical and used regularly by the passenger.

As illustrated in FIG. 4, the system 400 includes an acoustic event detector 410 (e.g., audio sensor) and an environmental condition detector 420 which includes a plurality of sensors including a particulate (e.g., PM 2.5) sensor 420a, a VOC sensor 420b, a humidity sensor 420c and a temperature sensor 420d. The system 400 also includes a remediation action determining device 430 which receives an acoustic event signal (e.g., wireless or wired signal) from the acoustic event detector 410 and a signal from the environmental condition detector 420, and determines a remediation action (e.g., an action intended to remedy a symptom of the passenger from whom the acoustic event (e.g., cough, sneeze, etc.) originated) based on an acoustic event detected by the acoustic event detector 410 and an environmental condition detected by the environmental condition detector 420.

The remediation action determining device 430 may include a processing device such as a computer, microprocessor device, etc. which executes instructions (e.g., software) stored on a storage medium (e.g., memory device included in the processing device or otherwise accessible by the processing device), in order to perform the features and functions of the remediation action determining device 430.

The remediation action determining device 430 may include an identifier module 430a which receives the acoustic event signal (e.g., wireless or wired signal) from the acoustic event detector 410, and identifies a type of the acoustic event detected. For example, the type identified by the identifier module 430a may include a symptom (e.g., cough, sneeze, breath, etc.), or a non-symptom (e.g., seat belt clicking, door closing, etc.)

The remediation action determining device 430 may also include a passenger mode detection module 430b (e.g., following voice-based passenger mode detection module), which receives an output from the identifier module 430a and based on the output (e.g., based on the type of acoustic event detected by the acoustic event detector 410) detects a passenger mode. The passenger mode detection module 430b may include a source detector 430b1 which detects the source (e.g., identifies the passenger from which the acoustic event originated) of the acoustic event, and a passenger distribution identification module 430b2 which identifies a passenger distribution (e.g., locations such as "front passenger seat", "driver seat", etc.) in the vehicle.

The remediation action determining device 430 may also include an in-vehicle air quality evaluation module 430c which receives a signal (e.g., wireless or wired signal) from the environmental condition detector 420, and evaluates the quality of the air in the vehicle. For example, the in-vehicle air quality evaluation module 430c may evaluate the amount of particulates (e.g., PM 2.5), the amount of VOC, the amount of humidity, and the temperature of the air inside the vehicle, and perform an air quality and profile-based impact analysis.

The remediation action determining device 430 may also include a profiling correlation builder and enhancer module 430d which receives an output of the source detector 430b1 (e.g., identity of the passenger) and an output of the in-vehicle air quality evaluation module 430c (e.g., an evaluation of the air quality in the vehicle), and based on these two outputs, builds and enhances a profiling correlation (e.g., acoustic profile) which correlates the acoustic event and passenger identity, with the air quality evaluation, and determines a remediation action based on the correlation.

In determining the remediation action, the profiling correlation builder and enhancer module 430d may consider a passenger type, a sensitivity of the passenger to the environment, whether the passenger has CRD, and so on. The profiling correlation builder and enhancer module 430d may also identify the source of the passenger's irritation (e.g., the environmental condition which is exacerbating the passenger's condition and causing the passenger to cough, wheeze, etc.), and also assign a confidence level to the data included in the profiling correlation.

The remediation action determining device 430 may also include voice identity matching and profiling module 430e which receives passenger distribution identification data from the passenger distribution identification module 430b2, and based on the passenger distribution identification data matches a passenger voice to a passenger of the vehicle. In particular, the voice identity matching and profiling module 430e includes a single passenger voice profiling module 430e1 which profiles a voice of a single passenger (e.g., the driver), and a multiple passenger voice profiling module 430e2 which profiles a voice of multiple passengers. The voice identity matching and profiling module 430e also includes a voice ID matching module 430e3 which matches a voice detected by the acoustic event detector 410 with a passenger identity, and stores the matching voice/passenger identity in a vehicle voice database 4300.

As illustrated in FIG. 4, the profiling correlation builder and enhancer module 430d may access the voice/passenger identity data which is stored in the vehicle voice database 430f, in order to build the profiling correlation.

It should be noted that the features of the remediation action determining device 430 (e.g., the profiling correlation builder and enhancer module 430d) may be implemented by a processing device such as a computer, processor, server, etc. executing instructions (e.g., software) to perform the functions of the features described herein.

Referring again to FIG. 4, the system 400 may also include a remediation action controller 440 which controls a remediation action that has been recommended by the profiling correlation that has been built/enhanced by the profiling correlation builder and enhancer module 430d. The remediation action controller 440, for example, may be considered an air quality manager which manages an air quality in the vehicle based on the recommended remediation action. The remediation action determining device 430 and the remediation action controller 440 (e.g., air quality manager) may be combined to form a symptom remedying device.

In particular, the remediation action controller 440 may include a recommended service action subcontroller 440a which may control a service to be provided to the vehicle in order to remedy a symptom of the passenger in the vehicle. For example, the recommended service action subcontroller 440a may perform a service on a device in the vehicle's HVAC system (e.g., humidifier, air purifier, etc.), or may arrange (e.g., via wireless communication) for service to be performed by an HVAC professional on the vehicle's HVAC system.

In particular, the recommended service action subcontroller 440a service the vehicle's air quality control system by adding assistant devices to the vehicle, based on a disease of a passenger as determined by the remediation action determination determining device 430. For example, as indicated in the table 450, where the remediation action determination determining device 430 has determined that the passenger has senile pneumonia, the recommended service action subcontroller 440a may add a humidifier to the vehicle's HVAC system, and so on.

The remediation action controller 440 may also include a recommended control action subcontroller 440a which performs a control operation in order to remedy the passenger's symptoms. For example, where the remediation action determination determining device 430 has recommended that a temperature of air in the cabin of the vehicle should be adjusted to remedy the passenger's symptoms, the recommended control action subcontroller 440a may control the vehicle's HVAC system in order to adjust the a temperature of air in the cabin of the vehicle, and so on.

The remediation action controller 440 may also include a recommended smarter home action subcontroller 440c. For example, where the remediation action determination determining device 430 has recommended that a temperature of air in the cabin of the vehicle should be adjusted to remedy the passenger's symptoms, the recommended control action subcontroller 440a may control the passenger's home HVAC system (e.g., via wireless communication) in order to adjust the a temperature of air in the passenger's home, and so on.

That is, in addition to the air quality of the vehicle, the air quality manager may also manage an air quality in another environment of the passenger, such as the passenger's home or office. That is, the system 400 may also include a wireless transceiver 435 which allows the recommended smarter home action subcontroller 440c to wirelessly communicate a recommended remediation action to an HVAC controller in the passenger's home or office so that the HVAC controller may adjust the HVAC system based on the recommended remediation action.

It should be noted that the recommended remediation action may be automatically taken by the system 400, or the system 400 can be connected to the vehicle's sound system to audibly communicate the recommendation to the passengers via the sound system, and/or connected to the vehicle's display (e.g., navigation display, etc.) to visually communicate the recommendation to the passengers via the display. This allows the passenger to decide whether to take the recommended remediation action.

Figure 5:
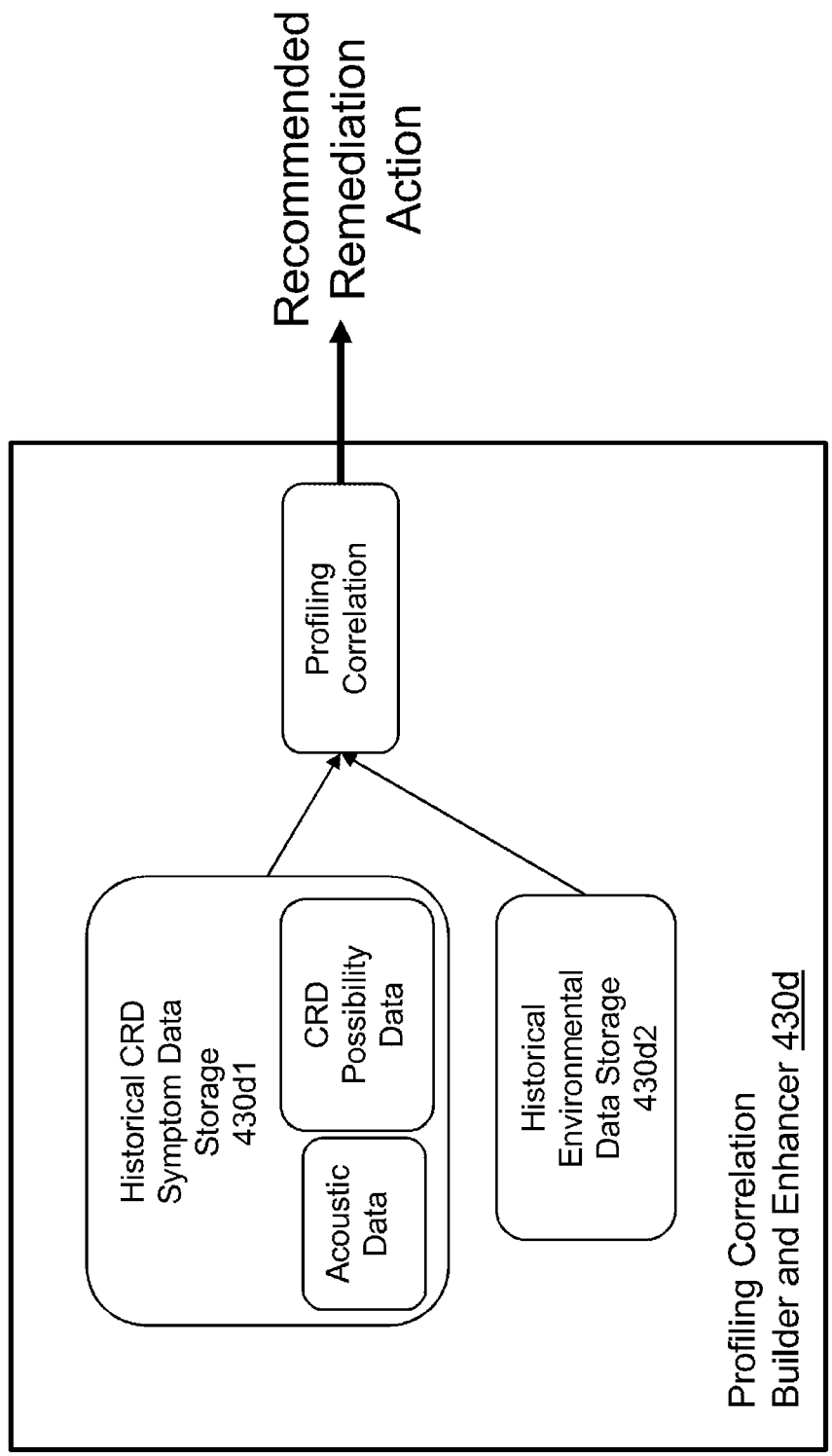
FIG. 5 illustrates a profiling correlation builder and enhancer 530d, according to an exemplary aspect of the present invention.

FIG. 5 illustrates a profiling correlation builder and enhancer 430d, according to an exemplary aspect of the present invention.

As illustrated in FIG. 5, the profiling correlation builder and enhancer 430d may include a historical CRD symptom data storage 430d1 which stores historical CRD symptom data (e.g., acoustic data and CRD possibility data), and a historical environmental data storage 430d2 which stores historical environmental data. The profiling correlation builder and enhancer 430d may use the historical CRD symptom data and the historical environmental data to build and/or enhance the profiling correlation, and then extract the recommended remediation action from the profiling correlation which is transmitted to the remediation action controller 440.

Table 2 below illustrates a profiling correlation which has been built and/or enhanced by the profiling correlation builder and enhancer 430*d*, according to an exemplary aspect of the present invention.

TABLE 2

| Diseases | Acoustic Feature | Risk Factor | Confidence Level | Recommended Action | Add Assistant Devices |
|---|---|---|---|---|---|
| Senile pneumonia | Breathing rate increases or breathing trapped | . . . | . . . | Close air conditioner | Humidifier |
| Lung cancer | High cough companion with trapped breathing | . . . | . . . | Purify air | Air purifier |
| Cough-type asthma | Paroxysmal cough | Humidity, temperature, air pollutants, pollen, etc. | . . . | Frequently replace air | Air conditioner filter |
| Upper respiratory tract obstruction | Cough asthmatic wheeze | . . . | . . . | Frequently open window for ventilation | Activated carbon |
| Chronic obstructive pulmonary disease (COPD) | Exhale breath trapped and coughing all the year round | Humidity, temperature, wind, PM2.5, VOC, etc. | . . . | Open window or air conditioner outside loop | Air purifier, humidifier or oxygen therapy. |

As illustrated in Table 2, the profiling correlation may include a chart which includes a disease column, acoustic feature column, risk factor column, confidence level column, recommended action (e.g., recommended remediation action) column and an add assistant device column. Then entries in each of these columns may be added and/or refined by the profiling correlation builder and enhancer 430*d*, based on data obtained from the in-vehicle air quality evaluation module 430*c*, the following voice-based passenger mode detection module 430*b* and the voice identity matching and profiling module 430*e*. The profiling correlation builder and enhancer 430*d* may extract one or more entries from the recommended action column, and transmit the extracted entries to the remediation action controller 440.

The profiling correlation builder and enhancer 430*d* may include, for example, an initial profiling correlation which is based on the population at large. This initial profiling correlation may serve as a starting point for the profiling correlation builder and enhancer 430*d* which enhances or "refines" the initial profiling correlation based on data received in the vehicle, in order to generate a personalized profiling correlation 700 which may be unique to each individual passenger.

The present invention may also include a remediation action monitor that may include data which is compiled by the remediation action storage device 430 and stored in the remediation action determining device 430 (e.g., in a storage medium accessible by a processing device of the remediation action determining device 430). The data may include, for example, a chart which includes columns identifying a passenger, action taken, time that action was taken, change in air quality as a result of action, and change in acoustic events detected as a result of action. The profiling correlation builder and enhancer 430*d* may utilize the remediation action monitor to monitor the effectiveness of the action taken based on a recommendation of the profiling correlation builder and enhancer 430*d*. For example, if the profiling correlation builder and enhancer 430*d* determines, based on the data obtained from the remediation action monitor, that the action taken was not sufficiently effective, the profiling correlation builder and enhancer 430*d* may revise the profiling correlation accordingly.

Figure 6:
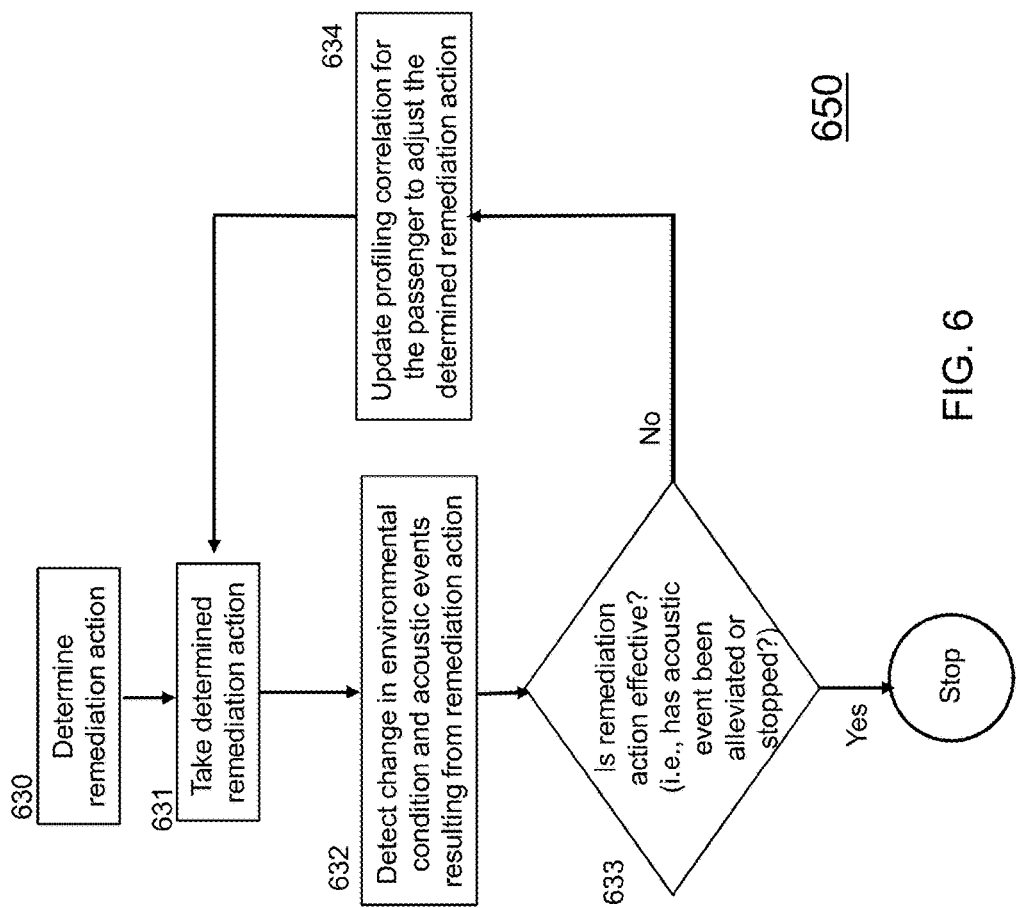
FIG. 6 illustrates a method 600 of monitoring a remediation action, according to an exemplary aspect of the present invention.

FIG. 6 illustrates a method 650 of monitoring a remediation action, according to an exemplary aspect of the present invention.

As illustrated in FIG. 6, the method 650 may include determining (630) a remediation action (similar to determining of the remediation action described above in FIG. 4), taking (631) the determined remediation action (e.g., increasing the air temperature in the vehicle, decreasing the humidity in the vehicle, etc.), detecting (632) a change in the environmental conditions and the acoustic events resulting from the remediation action, and determining (633) whether the remediation action is effective (i.e., determining whether the acoustic event been alleviated or stopped) based on the detected environmental conditions and the detected acoustic events. If the remediation action is determined to be effective, then the process stops, but if the remediation action is determined to not be effective, then the process updates (634) the profiling correlation for the passenger to adjust the determined remediation action, and then the process returns to taking (631) the newly determined remediation action.

Figure 7:
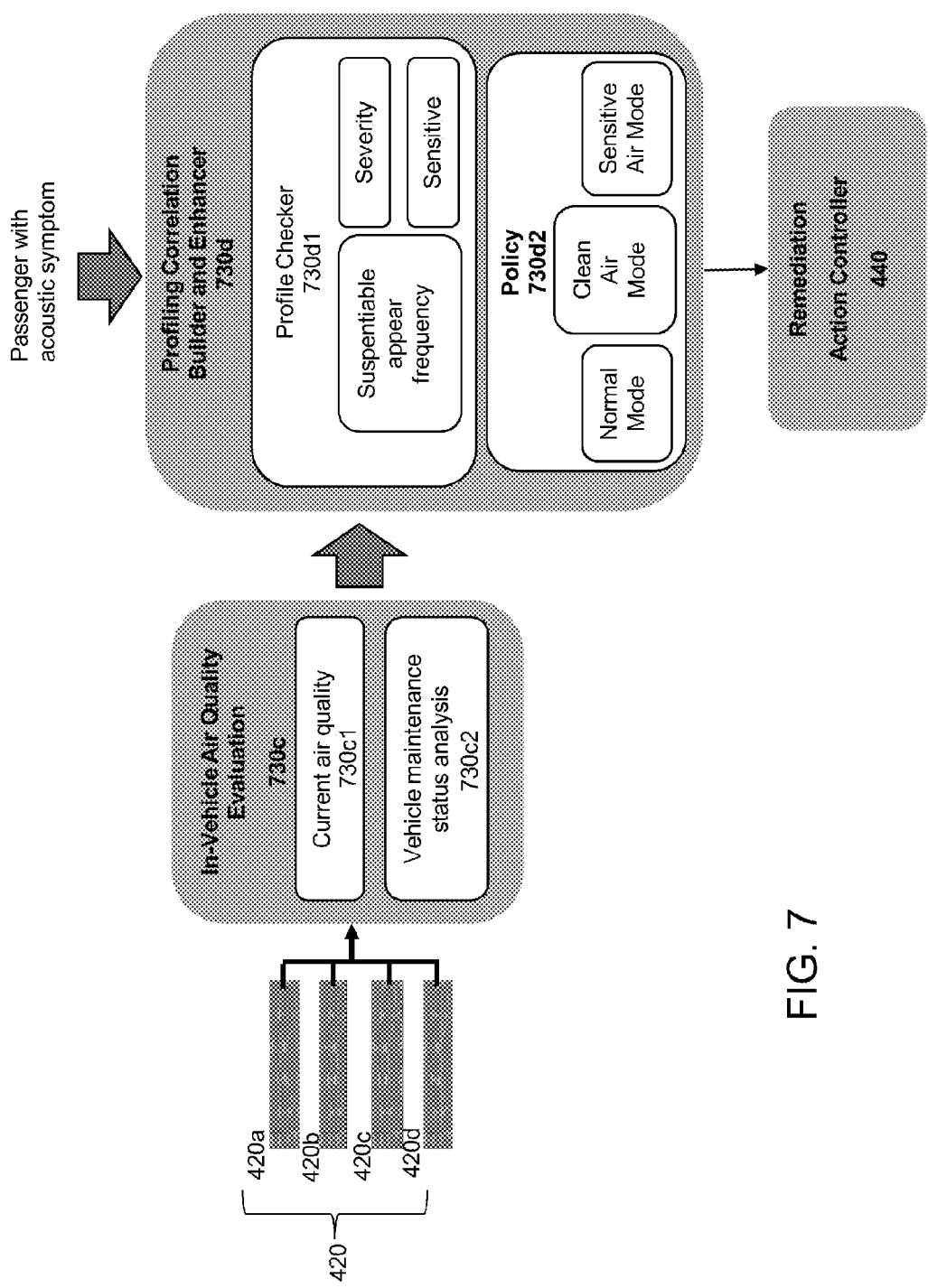
FIG. 7 illustrates an air quality evaluation module 730c and profiling builder and enhancer module 730d, according to another exemplary aspect of the present invention.

FIG. 7 illustrates an in-vehicle air quality evaluation module 730*c* and profiling builder and enhancer module 730*d*, according to another exemplary aspect of the present invention. The in-vehicle air quality evaluation module 730*c* may be utilized, for example, in the remediation action determining device 430 instead of the in-vehicle air quality evaluation module 430*c*. The in-vehicle air quality evaluation module 730*c* may be used by the system 400 to provide dynamic profile feature-based vehicle targeted control of the vehicle's heating and air conditioning system.

As illustrated in FIG. 7, the in-vehicle air quality evaluation module 730*c* includes a current air quality submodule 730*c*1 and vehicle maintenance status analysis module 730*c*2. The in-vehicle air quality evaluation module 730*c* receives environmental condition from the environmental condition detector 420, and based on the detected environmental condition, the current air quality and a vehicle maintenance status analysis, the in-vehicle air quality evaluation module 730c generates in-vehicle air quality evaluation information and transmits this information to the profiling builder and enhancer module 730d.

The profiling builder and enhancer module 730d includes a profile checker 730d1 which checks the profile correlation (e.g., profile correlation 700) to determine a severity of a passenger's CRD, the sensitivity of the passenger (e.g., to temperature, humidity, etc.), and checks and a policy module 730d2 to determine, for example, an operating mode (e.g., normal mode, clean air mode, sensitive air mode) of the vehicle's heating and air conditioning system. The profiling builder and enhancer module 730d receives passenger information on the passenger with an acoustic system (e.g., from the following voice-based passenger mode detection module 430b), and determines a remediation action based on the passenger information, the determination of the profile checker 730d1 and the determination of the policy module 730d2), and outputs the remediation action to the remediation action controller 440 which effects the remediation action (e.g., controls the vehicle's heating and air conditioning system to increase a temperature, reduce a humidity, etc.).

Figure 8:
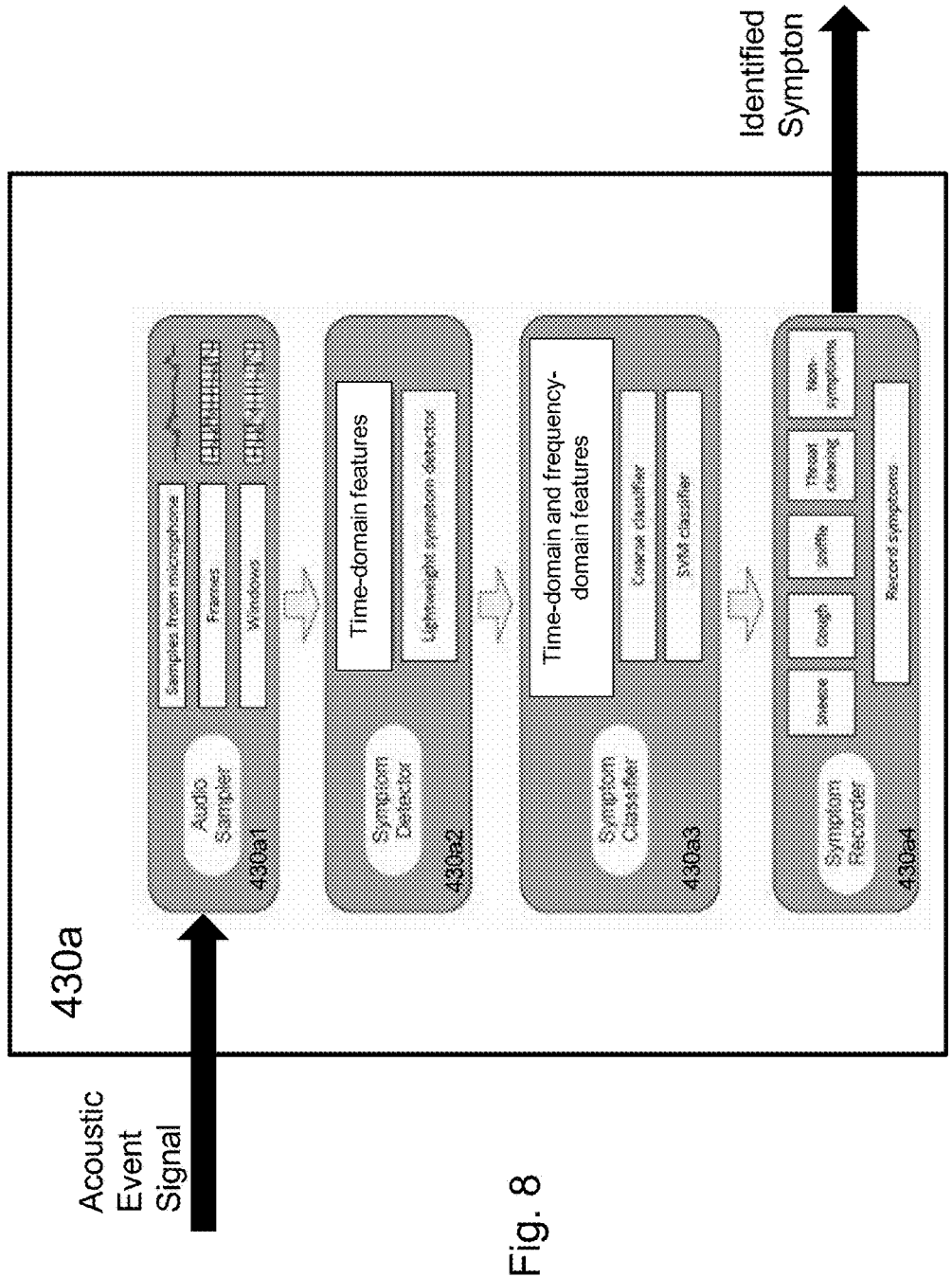
FIG. 8 is a more detailed illustration of the identifier module 530a, according to another exemplary aspect of the present invention.

FIG. 8 depicts another example of the identifier module 430a of FIG. 4 in accordance with the present invention. The identifier module 430a may provide for accurate symptom recognition in the vehicle based on the detected acoustic signal.

As illustrated in FIG. 8, the identifier module 430a may include an audio sampler 430a1 which receives the acoustic event signal from the acoustic event detector 410 (e.g., a microphone), samples the acoustic event signal and divides the acoustic event signal into frames and windows for analysis.

The identifier module 430a may also include a symptom detector 430a2 which receives an output of the audio sampler 430a1 and detects a symptom in the output. In particular, the symptom detector 430a2 may analyze the output for a time-domain features, and use a lightweight symptom detector to detect a symptom.

The identifier module 430a may also include a symptom classifier 430a3 which receives an output (e.g., symptom) of the symptom detector 430a2, and classifies the symptom in the output. In particular, the symptom classifier 430a3 may analyze the symptom for a time-domain and frequency domain feature, and use a coarse classifier and support vector machine (SVM) classifier to classify the symptom.

The identifier module 430a may also include a symptom recorder 430a4 which receives the symptom and symptom classification from the symptom classifier 430a3, and records (e.g., stores in a memory device) the symptom according to its classification (e.g., sneeze, cough, sniffle, throat clearing). The identifier module 430a may then transmit the symptom and symptom classification from the symptom recorder 430a4 to the following voice-based passenger mode detection module 430b.

It should be noted that an operation of the identifier module 430a (e.g., the manner in which the module distinguishes a symptom from other noises in the vehicle) may be different depending on conditions inside the vehicle. For example, if the radio is on in the vehicle, then the identifier module 430a may utilize a different filtering technique than if the radio is off in the vehicle. Other conditions influencing an operation of the identifier module 430a may include the windows being open, a high level of the fan of the heating and air conditioning system, a high level revolutions per minute (RPM) of the engine, rainfall on the windshield wipers being on, etc. Thus, the identifier module 430a may be configured to detect these conditions and filter them out of the acoustic event signal, so that these conditions do not affect an identifying operation in the identifier module 430a.

By way of example only, Table 3 below illustrates an impact factor comparison.

TABLE 3

|  | Reverberation | Background | Attenuation | SNR |
|---|---|---|---|---|
| Vehicular Space | Predictable | Predictable | Little | High |
| Office Space | Unpredictable | Unpredictable | Large | Low |
| Home Space | Unpredictable | Unpredictable | Large | Low |

As illustrated in Table 3, the values of the impact factors, which include reverberation, background, attenuation and signal-to-noise ratio (SNR), suggest that a vehicular space provides a more a more predictable reverberation and background, with relatively less attenuation and a higher SNR, indicating that the vehicular space offers several advantages over the office space and home space for detecting and remedying a symptom (e.g., CRD symptom).

By way of further example only, enclosed below is a chart which describes an exemplary symptom recognition performance, in accordance with an embodiment of the present invention.

TABLE 5

| Symptom | TPR | PPV |
|---|---|---|
| Sneeze | 0.836 | 0.910 |
| Cough | 0.831 | 0.866 |
| Sniffle | 0.824 | 0.827 |
| Throat clearing | 0.867 | 0.914 |
| Non-symptoms | 0.991 | 0.985 |

As illustrated in Table 4, the values for the true positive rate (TPR) and positive predictive value (PPV) in a system 400 in a vehicular space suggest that a vehicular space supports the studying of a correlation between respiratory symptoms and acoustic events (e.g., sound).

Referring to FIGS. 1-8, another aspect of the present invention is directed to a computer program product which may include, for example, a computer readable storage medium (hereinafter, the "storage medium") that may store computer readable program instructions (hereinafter, the "computer program" or "instructions") for performing the features and functions of the method 100 of determining a remediation action, and a system for determining a remediation action 200, 400 (e.g., memory included in the remediation action storage device 430). That is, the storage medium may store the instructions thereon for causing a processing device (e.g., computer, instruction execution device, computing device, computer processor, central processing unit (CPU), microprocessor, etc.) to perform a feature or function of the present invention.

The storage medium can be a tangible device that can retain and store the instructions for execution by the processing device. The storage medium may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

The storage medium, as used herein, should not be construed as merely being a "transitory signal" such as a radio wave or other freely propagating electromagnetic wave, an electromagnetic wave propagating through a waveguide or other transmission media (e.g., light pulses passing through a fiber-optic cable), or an electrical signal transmitted through a wire.

The processing device can access the instructions on the storage medium. Alternatively, the processing device can access (e.g., download) the instructions from an external computer or external storage device via a network such as the Internet, a local area network, a wide area network and/or a wireless network.

The network may include, for example, copper transmission cables, optical transmission fibers, wireless transmission, routers, firewalls, switches, gateway computers and/or edge servers. For example, the processing device may include a network adapter card or network interface which receives the instructions from the network and forwards the instructions to the storage medium within the processing device which stores the instructions.

The instructions for performing the features and functions of the present invention may include, for example, assembler instructions, instruction-set-architecture (ISA) instructions, machine instructions, machine dependent instructions, microcode, firmware instructions, state-setting data, or either source code or object code written in one or more programming languages (or combination of programming languages), including an object oriented programming language such as Java, Smalltalk, C++ or the like, and conventional procedural programming languages, such as the "C" programming language or similar programming languages.

The instructions may execute entirely on the processing device (e.g., a user's computer), partly on the processing device, as a stand-alone software package, partly on the processing device and partly on a remote computer or entirely on the remote computer or a server. For example, the instructions may execute on a remote computer which is connected to the processing device (e.g., user's computer) through a network such as a local area network (LAN) or a wide area network (WAN), or may execute on an external computer which is connected to the processing device through the Internet using an Internet Service Provider.

The processing device may include, for example, electronic circuitry including, for example, programmable logic circuitry, field-programmable gate arrays (FPGA), or programmable logic arrays (PLA) that may execute the instructions by utilizing state information of the instructions to personalize the electronic circuitry, in order to perform a feature or function of the present invention.

It should be noted that the features and functions of the present invention which are described above with reference to FIGS. 1-8 may be implemented by the processing device executing the instructions. That is, each block of the flowchart illustrations and/or block diagrams, and combinations of blocks in the flowchart illustrations and/or block diagrams, can be implemented by processing device executing the instructions.

The instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

That is, the instructions may be executed by a processing device to cause a series of operational steps to be performed by the processing device to produce a computer-implemented process, so that the executed instructions implement the features/functions/acts described above with respect to the flowchart and/or block diagram block or blocks of FIGS. 1-8.

Thus, the flowchart and block diagrams in the FIGS. 1-8 illustrate not only a method, system, apparatus or device, but also illustrate the architecture, functionality, and operation of the processing device executing the instructions. In this regard, each block in the flowchart or block diagrams may represent a module, segment, or portion of the instructions, which comprises one or more executable instructions for implementing the specified logical function(s). In some alternative implementations, the features or functions in the block may occur out of the order noted in the figures.

For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 9:
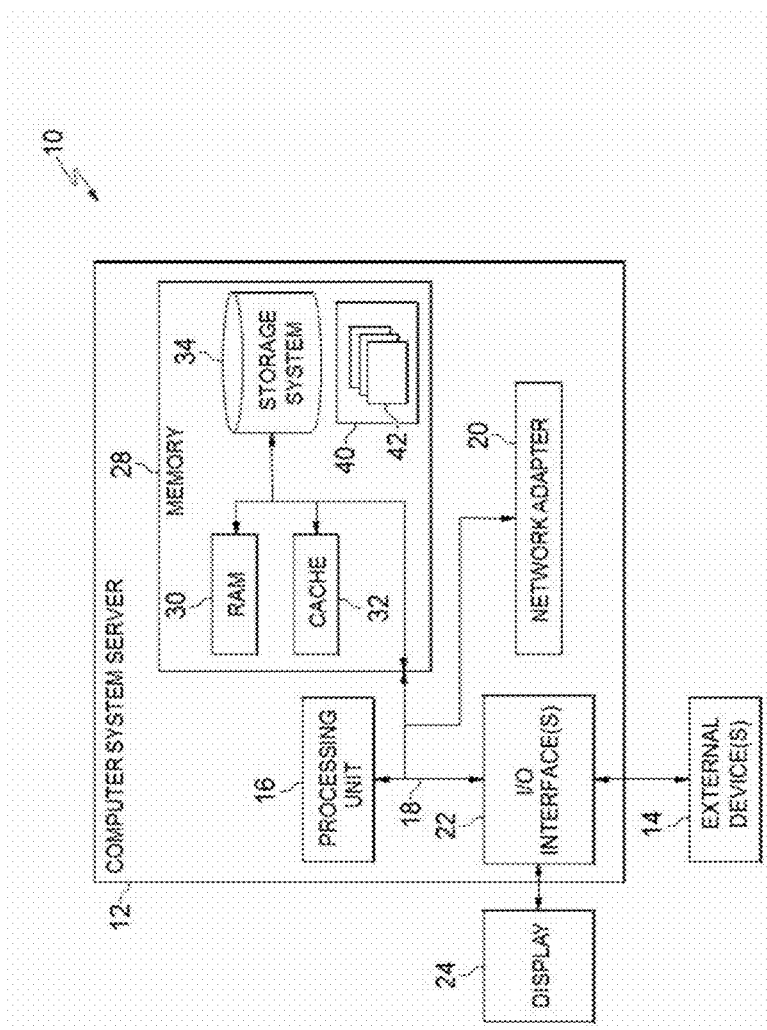
FIG. 9 depicts a cloud computing node according to an exemplary aspect of the present invention.
Figure 11:
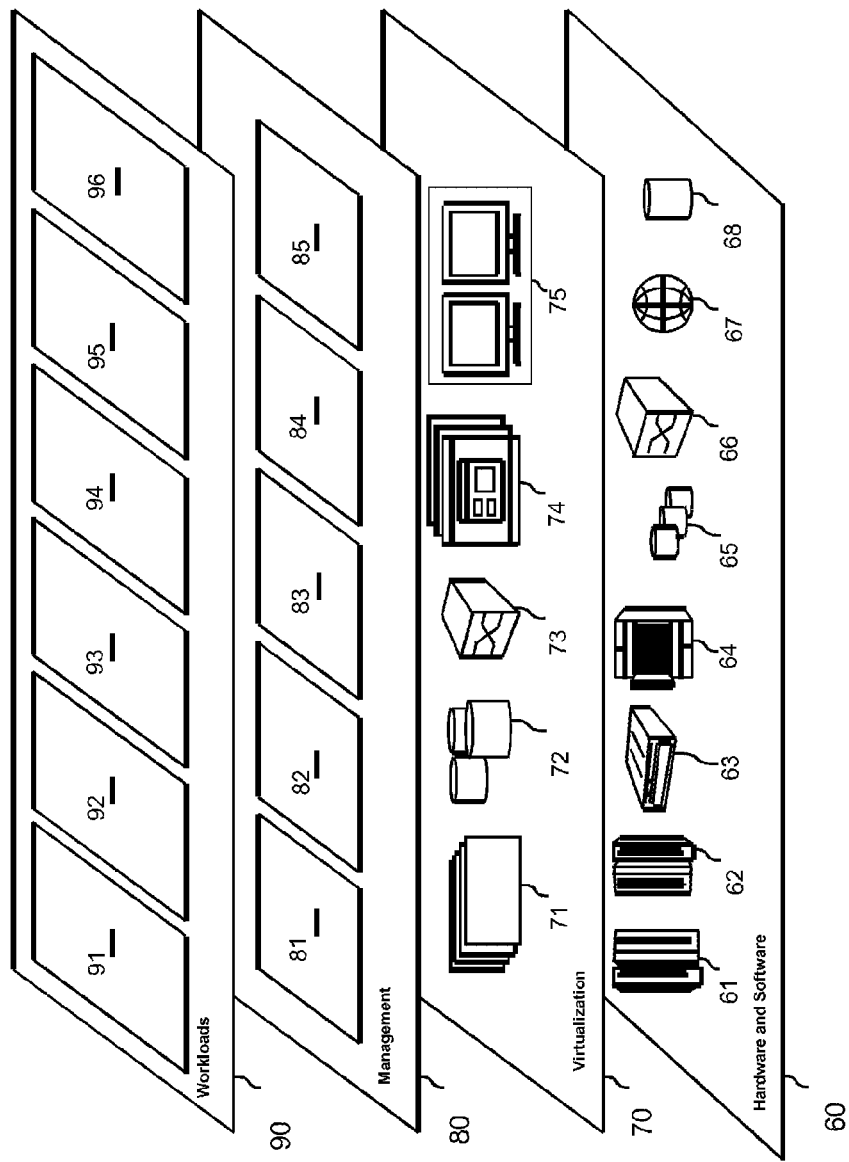
FIG. 11 depicts abstraction model layers according to an exemplary aspect of the present invention.

Referring again to the drawings, FIGS. 9-11 illustrate other exemplary aspects of the present invention.

It is to be understood that although this disclosure includes a detailed description on cloud computing, implementation of the teachings recited herein are not limited to a cloud computing environment. Instead, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 9, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring again to FIG. 9, computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media. System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external circuits 14 such as a keyboard, a pointing circuit, a display 24, etc.; one or more circuits that enable a user to interact with computer system/server 12; and/or any circuits (e.g., network card, modem, etc.) that enable computer system/server 12 to communicate with one or more other computing circuits. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Referring now to FIG. 10, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof.

This allows cloud computing environment 50 to offer infrastructure, platforms and/or software as services for which a cloud consumer does not need to maintain resources on a local computing device. It is understood that the types of computing devices 54A-N shown in FIG. 13 are intended to be illustrative only and that computing nodes 10 and cloud computing environment 50 can communicate with any type of computerized device over any type of network and/or network addressable connection (e.g., using a web browser).

Referring now to FIG. 11, a set of functional abstraction layers provided by cloud computing environment 50 (FIG. 10) is shown. It should be understood in advance that the components, layers, and functions shown in FIG. 11 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a remediation action determining function 96 in accordance with the present invention.

Exemplary aspects of the present invention may help alleviate or stop a symptom (e.g., a CRD symptom) of a passenger in the vehicle.

While the invention has been described in terms of one or more embodiments, those skilled in the art will recognize that the invention can be practiced with modification within the spirit and scope of the appended claims. Specifically, one of ordinary skill in the art will understand that the drawings herein are meant to be illustrative, and the design of the inventive method and system is not limited to that disclosed herein but may be modified within the spirit and scope of the present invention.

Further, Applicant's intent is to encompass the equivalents of all claim elements, and no amendment to any claim the present application should be construed as a disclaimer of any interest in or right to an equivalent of any element or feature of the amended claim.

What is claimed is:

1. A computer-implemented method of determining a remediation action, the method comprising:
   detecting an acoustic event in a vehicle;
   detecting an environmental condition in the vehicle;
   detecting a respiratory disease symptom of a passenger in the vehicle based on the detected acoustic event;
   correlating the detected respiratory disease symptom with the detected environmental condition in the vehicle; and
   determining a remediation action for the detected respiratory disease symptom.

2. The method of claim 1, wherein the detecting of the environmental condition is performed in response to the acoustic event detector detecting the acoustic event.

3. The method of claim 1, wherein the detecting of the acoustic event is performed by an acoustic event detector comprising an audio sensor.

4. The method of claim 1, wherein the detecting of the environmental condition comprises detecting in the vehicle an amount of particulate matter (PM), an amount of volatile organic compounds (VOCs), a humidity and a temperature.

5. The method of claim 4, wherein the detecting of the environmental condition is performed by an environmental condition detector comprising one of a PM sensor, a VOC sensor, a humidity sensor and a temperature sensor.

6. The method of claim 1, wherein the acoustic event comprises at least one of the passenger coughing, the passenger sneezing, the passenger wheezing, the passenger sniffing and the passenger clearing his throat, the passenger using a nasally voice, the passenger taking shallow breaths, and the passenger taking deep breaths.

7. The method of claim 1, further comprising:
   tracking an effect of the remediation action on acoustic events detected.

8. The method of claim 7, further comprising:
   refining a remediation action determination based on the tracking of the effect of the remediation action.

9. The method of claim 1, further comprising:
   managing an air quality in the vehicle based on the determined remediation action.

10. The method of claim 9, wherein the managing of the air quality comprises managing the air quality in the vehicle by at least one of adjusting an amount of particulate matter (PM) in air in the vehicle, adjusting an amount of volatile organic compounds (VOCs) in the air, adjusting a humidity in the air, and adjusting a temperature of the air.

11. The method of claim 10, wherein the managing of the air quality is performed by an air quality manager which is formed in a heating and cooling system of the vehicle.

12. The method of claim 10, further comprising:
    storing a passenger profile which relates the determined remediation action with passenger information of the passenger,
    wherein the managing of the air quality comprises managing the air quality in the vehicle based on the passenger profile.

13. A system for determining a remediation action, the system comprising:
    an acoustic event detector for detecting an acoustic event in a vehicle;
    an environmental condition detector for detecting an environmental condition; and
    a remediation action determining device for:
      detecting a respiratory disease symptom of a passenger in the vehicle based on a detected acoustic event;
      correlating a detected respiratory disease symptom with the detected environmental condition in the vehicle; and
      determining a remediation action for the detected respiratory disease symptom.

14. The system of claim 13, wherein the environmental condition detector detects the environmental condition in response to the acoustic event detector detecting the acoustic event.

15. The system of claim 13, wherein the acoustic event detector comprises an audio sensor.

16. The system of claim 13, wherein the environmental condition comprises an amount of particulate matter (PM), an amount of volatile organic compounds (VOCs), a humidity and a temperature.

17. The system of claim 16, wherein the environmental condition detector comprises one of a PM sensor, a VOC sensor, a humidity sensor and a temperature sensor.

18. The system of claim 13, wherein the remediation action determining device:
    recommends the determined remediation action to the passenger;
    tracks an effect of the remediation action based on the detected acoustic event; and
    refines a remediation action determination based on the tracking of the effect of the remediation action.

19. The system of claim 13, further comprising:
    an air quality manager for managing an air quality in the vehicle based on the recommended remediation action.

20. A computer program product for determining a remediation action, the computer program product comprising a computer readable storage medium having program instructions embodied therewith, the program instructions executable by a computer to cause a method of, the computer to:
    detect an acoustic event in a vehicle;
    detect an environmental condition in the vehicle;
    detect a respiratory disease symptom of a passenger in the vehicle based on a detected acoustic event;
    correlate the detected respiratory disease symptom with the detected environmental condition in the vehicle; and
    determine a remediation action for the detected respiratory disease symptom.

* * * * *